(12) United States Patent
Salisbury

(10) Patent No.: US 8,519,181 B2
(45) Date of Patent: Aug. 27, 2013

(54) PREPARATION OF ACETIC ACID

(75) Inventor: Brian A. Salisbury, Oxford, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 328 days.

(21) Appl. No.: 12/798,598

(22) Filed: Apr. 7, 2010

(65) Prior Publication Data

US 2011/0251422 A1 Oct. 13, 2011

(51) Int. Cl.
*C07C 51/12* (2006.01)

(52) U.S. Cl.
USPC ............................................. 562/519

(58) Field of Classification Search
CPC ...................................................... C07C 51/12
See application file for complete search history.

(56) References Cited

U.S. PATENT DOCUMENTS

| 5,175,362 | A | * | 12/1992 | Fillers et al. ................ 562/607 |
| 5,227,517 | A | * | 7/1993 | Waller ........................ 560/238 |
| 5,502,243 | A | * | 3/1996 | Waller et al. ................ 560/232 |
| 5,817,869 | A | | 10/1998 | Hinnenkamp et al. |
| 5,932,764 | A | | 8/1999 | Morris et al. |
| 6,667,418 | B2 | | 12/2003 | Broussard et al. |
| 7,524,988 | B2 | | 4/2009 | Harris et al. |

* cited by examiner

*Primary Examiner* — Paul A Zucker

(57) ABSTRACT

The disclosure relates to a process for the preparation of acetic acid. The process comprises reacting a decanter heavy, organic phase of an acetic acid production process with acetic anhydride to convert acetaldehyde in the decanter heavy, organic phase to ethylidene diacetate and separating it from the decanter heavy, organic phase. Ethylidene diacetate can be hydrolyzed to recover acetic acid.

13 Claims, No Drawings

PREPARATION OF ACETIC ACID

FIELD OF THE INVENTION

The invention relates to the preparation of acetic acid. More particularly, the invention relates to a process for removing acetaldehyde from the acetic acid production process.

BACKGROUND OF THE INVENTION

The carbonylation of methanol produces acetic acid:

$$CH_3OH + CO \rightarrow CH_3COOH$$

Prior to 1970, acetic acid was made using cobalt catalysts. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem with the original Monsanto process is that a large amount of water (about 14%) is needed to produce hydrogen in the reactor via the water-gas shift reaction (CO+ $H_2O \rightleftharpoons CO_2 + H_2$). 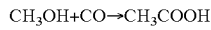 Water and hydrogen are needed to react with precipitated Rh(III) and inactive $[RhI_4(CO)_2]^-$ to regenerate the active Rh(I) catalyst. The large amount of water increases the amount of hydrogen iodide, which is highly corrosive and leads to engineering problems. Further, removing a large amount of water from the acetic acid product is costly.

In the late '70s, Celanese modified the Monsanto process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the late '90s, Lyondell Chemical Company (by its predecessors) developed a new rhodium carbonylation catalyst system that does not use iodide salt. The catalyst system uses a pentavalent Group VA oxide such as triphenyiphosphine oxide as a catalyst stabilizer. The Lyondell catalyst system not only reduces the amount of water needed but also increases the carbonylation rate and acetic acid yield. See U.S. Pat. No. 5,817,869.

One challenge still facing the industry is that lowering water concentration in the methanol carbonylation results in increased aldehyde formation. Methods for reducing aldehyde concentration in acetic acid are known. For instance, U.S. Pat. No. 6,667,418 discloses a method for reducing aldehydes by oxidizing them with air, hydrogen peroxide, and other free radical initiators in an integrated acetic acid production process at an elevated temperature. Introducing free radical initiators into acetic acid production process is inconvenient because free radical initiators are explosive. U.S. Pat. No. 7,524,988 discloses a method which comprises reacting an acetic acid stream containing aldehyde impurities with glycols to form corresponding dioxanes. The dioxanes are subsequently removed from the acetic acid by, e.g., distillation. However, the dioxanes are stable and the glycols thus cannot be easily recovered.

New methods for reducing aldehydes in acetic acid are needed. Ideally, the aldehyde can be effectively removed by forming a product which can be readily decomposed to recover the starting materials.

SUMMARY OF THE INVENTION

The invention relates to a process for removing acetaldehyde from the acetic acid production process. The process comprises reacting a stream of an acetic acid production process, which comprises methyl iodide and acetaldehyde, for instance, the decanter heavy, organic phase, with acetic anhydride to convert acetaldehyde to ethylidene diacetate and separating it from the stream.

In an embodiment, the process comprises reacting methanol and carbon monoxide in the presence of a carbonylation catalyst, a catalyst stabilizer, methyl iodide, water and methyl acetate to produce an acetic acid stream comprising the catalyst, the catalyst stabilizer, methyl iodide, methyl acetate, water, acetic acid, and acetaldehyde. At least a portion of the acetic acid stream is flashed to produce a vapor stream which comprises acetic acid, water, methyl acetate, methyl iodide and the acetaldehyde, and a liquid stream comprising the catalyst and the catalyst stabilizer. The vapor stream is distilled to an acetic acid product stream which comprises acetic acid and water, and an overhead stream which comprises methyl iodide, water, methyl acetate, acetic acid, and the acetaldehyde. The overhead stream is condensed in a decanter to produce a light, aqueous phase which comprises water, acetic acid, and methyl acetate, and a heavy, organic phase which comprises methyl iodide and the acetaldehyde. At least a portion of the heavy, organic phase is reacted with acetic anhydride to convert the acetaldehyde to ethylidene diacetate which is separated from the heavy, organic phase. The resultant heavy, organic phase, which is essentially free of acetaldehyde, is optionally recycled to the carbonylation.

DETAILED DESCRIPTION OF THE INVENTION

The carbonylation reaction is usually performed in the presence of a carbonylation catalyst and a catalyst stabilizer. Suitable carbonylation catalysts include those known in the acetic acid industry. Examples of suitable carbonylation catalysts include rhodium catalysts and iridium catalysts.

Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_3$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(C)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are chloride-free such as acetates.

Preferably, the reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydroysis/methanolysis of polyvinyl acetate can be used for the carbonylation reaction.

Preferably, the reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the acetic reactor and then reacts with carbon monoxide and water to give acetic acid and regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

An acetic acid product stream is withdrawn from the reactor and is separated, by a flash separation, into a liquid fraction comprising the catalyst and the catalyst stabilizer and a vapor fraction comprising the acetic acid product, the reactants, water, methyl iodide, and impurities generated during the carbonylation reaction including acetaldehyde. The liquid fraction is preferably recycled to the carbonylation reactor. The vapor fraction is then passed to a distillation column.

The distillation column, the so called "light ends distillation," separates an overhead comprising methyl iodide, water, methanol, methyl acetate, and acetaldehyde from an acetic acid stream comprising acetic acid, a small amount of water, and heavy impurities such as propionic acid. The acetic acid stream may be passed to a drying column to remove water and then be subjected to the so called "heavy ends distillation" to remove the heavy impurities.

The overhead from the light ends distillation preferably comprises from about 60 wt % to about 90 wt % of methyl iodide, from about 5 wt % to about 15 wt % of methyl acetate, from about 1 wt % to about 10 wt % of acetic acid, 1 wt % or less of water, from about 1 wt % to about 10 wt % of alkane impurities, and about 2 wt % or less of acetaldehyde based on the total weight of the overhead.

The overhead is condensed and separated in a decanter to a light, aqueous phase and a heavy, organic phase. The heavy, organic phase comprises methyl iodide and the acetaldehyde. The light, aqueous phase comprises water, acetic acid, and methyl acetate. The aqueous phase is preferably recycled to the reactor or to the light ends distillation.

According to the invention, at least a portion of the heavy, organic phase is reacted with acetic anhydride to convert the acetaldehyde to ethylidene diacetate. Preferably, about 5% to about 75% of the heavy, organic phase is reacted with acetic anhydride. More preferably, about 5% to about 50% of the heavy, organic phase is reacted with acetic anhydride. Ethylidene diacetate is separated from the heavy, organic phase by, e.g., distillation. The resultant heavy, organic phase, which is essentially free of acetaldehyde, can be directed to the decanter or the carbonylation reaction.

Preferably, the reaction of the heavy, organic phase with acetic anhydride is performed at a temperature within the range of about 20° C. to about 135° C. More preferably, the temperature is within the range of about 20° C. to about 50° C. Preferably, the treatment is performed in the presence of an acid catalyst. More preferably, the acid catalyst is an ion exchange resin.

Preferably, acetic anhydride is used in an amount within the range of about 1 equivalent to about 10 equivalents of acetaldehyde. More preferably, acetic anhydride is used in an amount within the range of about 2 equivalents to about 5 equivalents of acetaldehyde.

Ethylidene diacetate can be hydrolyzed by any known methods and the recovered acetic acid is preferably recycled to decanter or the light ends distillation.

The following example merely illustrates the invention. Those skilled in the art will recognize many variations that are within the spirit of the invention and scope of the claims.

EXAMPLE 1

A glass column is packed with Amberlyst® 15 (an acidic ion exchange resin, product of Sigma-Aldrich, 10 mL). The inlet of the column is attached to a static mixer which is fed by a small piston pump and a syringe pump. A decanter heavy, organic phase type solution, which contains 652 g methyl iodide, 10.01 g acetic acid, 60 g methyl acetate, 5.7 wt % of isooctane, 3.91 g acetaldehyde, and 10 g heptane, is loaded into a feed vessel for the piston pump. A 20-mL syringe is loaded with acetic anhydride and fitted to the syringe pump. The piston pump is set at a rate of 200 mL/hr. As the first drop of the solution is eluting from the column, the syringe pump containing the acetic anhydride is turned at rate of 6.5 mL/hr. Samples are obtained every ten minutes for 90 minutes and analyzed via gas chromatography for the presence of acetaldehyde. The samples show that acetaldehyde is completely converted to ethylidene diacetate after 10 minutes of reaction.

I claim:

1. A process comprising reacting a stream of an acetic acid production process, which comprises methyl iodide and acetaldehyde, with acetic anhydride in the presence of an acid catalyst comprising an ion exchange resin to convert acetaldehyde to ethylidene diacetate, and separating the ethylidene diacetate from the stream.

2. The process of claim 1, wherein the stream of the acetic acid production process is a decanter heavy, organic phase.

3. The process of claim 2, wherein the separation of the ethylidene diacetate from the decanter heavy, organic phase is by distillation.

4. The process of claim 3, comprising hydrolyzing the separated ethylidene diacetate to recover acetic acid.

5. A process for producing acetic acid, said process comprising:
   (a) reacting methanol and carbon monoxide in the presence of a carbonylation catalyst, a catalyst stabilizer, methyl iodide, water and methyl acetate to produce an acetic acid stream comprising the catalyst, the catalyst stabilizer, methyl iodide, methyl acetate, water, acetic acid, and acetaldehyde;
   (b) flashing at least a portion of the acetic acid stream to produce a vapor stream comprising acetic acid, water, methyl acetate, methyl iodide and acetaldehyde, and a liquid stream comprising the catalyst and the catalyst stabilizer;
   (c) separating the vapor stream by distillation into an acetic acid product stream comprising acetic acid and water, and an overhead stream comprising methyl iodide, water, methyl acetate, acetic acid, and acetaldehyde;
   (d) condensing the overhead stream to produce a light, aqueous phase comprising water, acetic acid, and methyl acetate, and a heavy, organic phase comprising methyl iodide and acetaldehyde;
   (e) reacting at least a portion of the heavy, organic phase with acetic anhydride in the presence of an acid catalyst comprising an ion exchange resin to convert acetaldehyde to ethylidene diacetate; and
   (f) separating the ethylidene diacetate from the heavy, organic phase by distillation.

6. The process of claim 5, comprising hydrolyzing the ethylidene diacetate to recover acetic acid.

7. The process of claim 6, comprising recycling the recovered acetic acid to step (d).

8. The process of claim 5, wherein the carbonylation catalyst is a rhodium catalyst.

9. The process of claim 5, wherein the catalyst stabilizer is selected from the group consisting of pentavalent Group VA oxides, metal iodide salts, and mixtures thereof.

10. The process of claim 9, wherein the catalyst stabilizer is a phosphine oxide.

11. The process of claim 10, wherein the catalyst stabilizer is triphenylphosphine oxide.

12. The process of claim 5, wherein the water concentration of step (a) is 6wt % or less based on the total weight of the acetic acid stream.

13. The process of claim 5, wherein step (e) occurs at a temperature of from about 20° C. to about 50° C.

* * * * *